US005628986A

United States Patent [19]
Sanker et al.

[11] Patent Number: 5,628,986
[45] Date of Patent: *May 13, 1997

[54] ORAL COMPOSITIONS

[75] Inventors: Lowell A. Sanker, Montgomery; James G. Upson, Springdale, both of Ohio

[73] Assignee: The Procter & Gamble Company, Cincinnati, Ohio

[*] Notice: The term of this patent shall not extend beyond the expiration date of Pat. No. 5,451,401.

[21] Appl. No.: 632,936

[22] Filed: Apr. 16, 1996

Related U.S. Application Data

[63] Continuation of Ser. No. 341,716, Nov. 18, 1994, abandoned.

[51] Int. Cl.⁶ .............. A61K 33/34; A61K 7/16; A23L 1/22; A23L 1/226
[52] U.S. Cl. .............. 424/49; 424/52; 424/57; 424/58; 424/630; 424/638; 426/534; 426/650; 426/3; 426/74; 514/103; 514/499; 514/500; 514/974
[58] Field of Search ............... 424/49–58, 630, 424/638; 426/534, 650; 514/103, 499, 500, 974

[56] References Cited

U.S. PATENT DOCUMENTS

| 3,780,190 | 12/1973 | Kracauer | 426/213 |
|---|---|---|---|
| 4,045,290 | 8/1977 | Bulbenko et al. | 195/99 |
| 4,258,072 | 3/1981 | Eguchi et al. | 426/537 |
| 4,472,447 | 9/1984 | Mizutani et al. | 426/537 |
| 4,826,824 | 5/1989 | Schiffman | 514/47 |
| 4,879,130 | 11/1989 | Heyland et al. | 426/533 |
| 5,216,945 | 6/1993 | Heyland et al. | 99/348 |
| 5,244,651 | 9/1993 | Kayane et al. | 424/42 |
| 5,260,051 | 11/1993 | Cho | 424/57 |
| 5,389,360 | 2/1995 | Mobley et al. | 424/49 |

FOREIGN PATENT DOCUMENTS

| 902690 | 10/1985 | Belgium . | |
|---|---|---|---|
| 4216078 | 5/1992 | Denmark . | |
| 512599 | 11/1992 | European Pat. Off. | A61K 7/16 |
| 555864 | 8/1993 | European Pat. Off. | A61K 7/16 |
| 569666 | 11/1993 | European Pat. Off. | A61K 7/16 |
| 290352 | 12/1989 | Germany . | |
| 011586 | 3/1959 | Japan . | |
| 43-31559 | 4/1968 | Japan . | |
| 7009 | 9/1970 | Japan . | |
| 53020462 | 8/1976 | Japan . | |
| 58-129958 | 1/1982 | Japan . | |
| 01222755 | 3/1988 | Japan . | |
| 63-157545 | 6/1988 | Japan . | |
| 1115557 | 5/1989 | Japan . | |
| 04346748 | 5/1991 | Japan . | |
| 9209480 | 9/1990 | Rep. of Korea . | |
| 1658975 | 10/1988 | Switzerland . | |
| 1806199 | 5/1991 | Switzerland . | |
| 1806200 | 5/1991 | Switzerland . | |
| WO9401005 | 7/1992 | WIPO . | |
| WO93/18741 | 9/1993 | WIPO | A61K 7/16 |
| WO95/11262 | 9/1994 | WIPO | A61K 7/16 |
| WO95/07684 | 3/1995 | WIPO | A61K 7/16 |
| WO95/07683 | 3/1995 | WIPO | A61K 7/16 |

OTHER PUBLICATIONS

"Some Derivatives of 4–t–Butylcyclohexyl and 1–Menthol–Phosphorochloridates", Phosphorus and Sulfur 1978, vol. 5, pp. 1–14 Cremlyn et al phosphorylated L–menthol.

"Introduction to Organic Chemistry", Streitwieser, A., Third edition, Macmillan Publishing Company, 1985, pp. 776–780. pyrophosphoric acid esters of alcohols.

Hauptwerk of Beilstein, 3rd Supp., 6th vol., pp. 165–167, 539, 1905.

U.S. application No. 08/360,191, Nelson et al., filed Dec. 10, 1994.

U.S. application No. 08/123,484, Eis et al., filed Sep. 17, 1993.

U.S. application No. 08/123,494, Nelson et al., filed Sep. 17, 1993.

U.S. application No. 08/306,868, Shahidi, filed Sep. 15, 1994.

*Primary Examiner*—Shep K. Rose
*Attorney, Agent, or Firm*—Mary Catherine Poland; Douglas C. Mohl; David K. Dabbiere

[57] ABSTRACT

Disclosed are oral compositions such as toothpastes, mouthrinses, liquid dentifrices, lozenges and gums containing at least one phosphate derivative and a copper source.

11 Claims, No Drawings

ORAL COMPOSITIONS

This is a continuation of application Ser. No. 08/341,716, filed on Nov. 18, 1994 now abandoned.

TECHNICAL FIELD

The present invention relates to oral compositions which provide antiplaque and antigingivitis benefits as well as being effective against other anaerobic infections of the mouth.

BACKGROUND OF THE INVENTION

Plaque induced diseases, including periodontitis and gingivitis, are believed to involve anaerobic bacterial infections. Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

The use of copper compounds in oral products have been widely published. One such reference, U.S. Pat. No. 4,332,791, issued Jun. 1, 1982 to Raaf et al., describes combinations containing copper salts in dentifrice compositions employing a silica abrasive. Similar references include U.S. Pat. No. 4,652,444, issued Mar. 14, 1987, to Maurer and U.S. patent application Ser. No. 08/096,535 to Mobley et al., filed Jul. 22, 1993, each further describing the use of copper compounds in oral care products.

An important disadvantage of these compounds, however, relates to the unpleasant aftertaste associated with their oral use. The importance of such a disadvantage becomes apparent when viewed in light of consumer satisfaction. Products with poor flavor, or unpleasant after-tastes may limit consumer satisfaction and, eventually, consumer usage.

The present inventors have discovered that the compositions of the present invention which contain copper compounds along with certain phosphate derivatives, provide improved tasting, antiplaque/antigingivitis compositions. Additionally, the present inventors have found that incorporating such phosphate derivatives provides improved actual and/or perceived efficacy of the resultant compositions. Further, these phosphate derivatives result in oral compositions providing a delayed flavor onset.

It is therefore an object of the present invention is to provide improved copper containing, oral compositions comprising a combination of phosphate derivatives.

Another object of the present invention is to provide good-tasting oral compositions effective in preventing and treating diseases of the oral cavity and preventing mouth odor.

A further object of the present invention is to provide methods for preventing and treating diseases of the oral cavity.

These and other objects will become readily apparent from the disclosure which follows.

All percentages and ratios used herein are by weight unless otherwise specified. Also, all measurements referred to herein are made at 25° C. in the composition unless otherwise specified.

SUMMARY OF THE INVENTION

The present invention relates to oral compositions, comprising:

a) from about 0.001% to about 25% of at least one phosphate derivative having the structure:

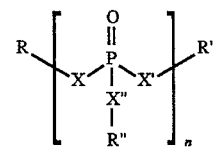

wherein R is selected from the group consisting of a coolant component, a sweetener component, and a flavorant component;
wherein R' and R" are independently selected from the group consisting of R, an adherent component, $M^+$, $M^{++}$, $C^+$, and hydrogen;
wherein X, X', X" are independently selected from the group consisting of oxygen, nitrogen, and sulfur;
wherein n is an integer from 1 to 3;

b) a safe and effective amount of a copper ion source; and c) a pharmaceutically acceptable oral carrier.

The present invention also relates to the above compositions further comprising a flavoring agent.

The present invention further relates to methods of treating or preventing diseases of the oral cavity.

By "oral composition," as used herein, means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "pharmaceutically acceptable oral carrier," as used herein, means a suitable vehicle which can be used to apply the present compositions to the oral cavity in a safe and effective manner.

All levels and ratios are by weight of the total composition, unless otherwise indicated. Additionally, all measurements are made at 25° C. unless otherwise specified.

DETAILED DESCRIPTION OF THE INVENTION

The essential as well as optional components of the compositions of the present invention are described in the following paragraphs.

ESSENTIAL COMPONENTS

Phosphate Derivatives

The compositions of the present invention contain one or more phosphate derivatives. These compounds may be formulated by phosphorylating at least one coolant, sweetener or flavorant component using conventional phosphorylating methods such as those disclosed in Streitwieser, A., Jr. and Heathcock, C. H., *Introduction to Organic Chemistry* (Macmillan Publishing Company, N.Y. 1985) pp. 776–780 and, more specifically, Cremlyn, R. J. W.; Ellam, R. M; and Akhtar, N., "Some Derivatives of 4-t-butylcyclohexyl and 1-menthol-phosphorochloridates" *Phosphorus and Sulfur* (Gordon and Breach Science Publishers Ltd., 1978) Vol. 5, pp. 1–14, both of which are herein incorporated by reference. These compounds also include linking at least one coolant, sweetener or flavorant component to an adherent component via a phosphate bridge. In addition, pyrophosphate and triphosphate groupings may be substituted for the phosphate group. Coolant, flavorant, or adherent components may also be linked to phosphorous via two functional groups or attachment sites. Furthermore, the phosphate derivatives described above may be bound via Coulom-bic interaction with charged compounds or materials, including polymers.

The present compositions may deliver the desired coolant, flavorant and/or sweetener qualities through the action of the phosphate derivative itself. The compositions may also provide a sustained or delayed effect since release of the coolant, flavorant and/or sweetener component from the molecule does not occur until cleavage of the phosphate from the coolant, flavorant and/or sweetener by phosphatase enzymes. Without being limited by theory, it is believed that this sustained or delayed release profile provides improved actual and/or perceived efficacy. The phosphatase enzymes may include, but are not limited to, acidic, basic, or pyrophosphatases.

The term "coolant component" as used herein refers to coolant compounds having a hydroxy, amino, or thiol functionality which is capable of forming an ester, amido, or thioester linkage with a phosphorus(V) atom. Preferred coolant components are selected from the group consisting of menthol, 3-1-menthoxypropane-1,2-diol (TK-10 supplied by Takasago Perfumery Co., Ltd., Tokyo, Japan), menthone glycerol acetal ("MGA"), N-ethyl-p-menthane-3-carboxamide (WS-3 supplied by Sterling Organics), N,2,3-trimethyl-2-isopropylbutanamide (WS-23 supplied by SCM Glidco Organics) or menthyl lactate. While the terms "menthol" and "menthyl" as used herein can include the dextro- or levo-rotatory isomers of these compounds or racemic mixtures thereof, the preferred embodiments of the present invention incorporate the levorotatory isomers.

The term "flavorant component" as used herein refers to flavorant chemicals having a hydroxy, amino, or thiol functionality which is capable of forming either an ester, amido, or thioester linkage with a phosphorus(V) atom. Flavorant chemicals suitable for use in the present invention include hexanol, octanol, decanol, geranolol, ethyl maltol, parahydroxy phenylbutanone, phenyl ethyl alcohol, thymol, eugenol, eucalyptol, methyl salicylate, ethyl vanillin, vanillin, cinnamaldehyde glycerol acetal ("CGA"), or linalool. Further examples of suitable chemical flavorants are described in S. Arctander, *Perfume and Flavor Chemicals*, (1969) and Allure Publishing Corporation's *Flavor and Fragrance Materials*, (1993), both of which are herein incorporated by reference.

The term "sweetener component" as used herein refers to sweetener compounds having a hydroxy, amino, or thiol functionality which is capable of forming either an ester, amido, or thioester linkage with a phosphorus(V) atom. Preferred sweetener components are saccharin, xylitol, mannitol, sorbitol, acesulfame K, aspartame, and neohesperidin dihydrochalcone.

The term "adherent component" as used herein refers to either monomers, oligomers, or polymers having hydroxy, amino, or thiol functionalities which are capable of forming either ester amido, or thioester linkages with phosphorus(V) atoms. The monomers, oligomers, or polymers may also possess additional hydroxy, amino, or thiol groups which may either remain unsubstituted or be linked via ester amido, or thioester linkages to a phosphorus(V) atom which is also attached to a coolant, flavor, or active portion. Preferred compounds are selected from the group consisting of C12–C18 diacyl glycerol, partially hydrolyzed vinyl acetate/ethylene copolymer, cellulose, chitin, glucosamine, silica gel, glycerol, and lower alkyl vinyl ether-maleic acids.

The terms "M+" and "M++" as used herein refer to physiologically relevant metal cations. The phrase "physiologically relevant metal cations" as used herein refers to metal cations that are significant to the organic or bodily processes of a human or lower animal. Preferred "M+" cations are sodium and potassium. Preferred "M++" cations are calcium, zinc, magnesium, manganese, copper, and stannous.

The term "C+" as used herein refers to a cation. A cation as used herein refers to cations that contain positively charged nitrogen, phosphorus, oxygen, or sulfur atoms. Such cations may contain more than one positively-charged site and in the case of oligomers or polymers containing nitrogen, phosphorus, oxygen, or sulfur atoms, many positively-charged centers may exist. Preferred cations include ammonium, protonated amines such as protonated glucosamine, and partially or fully protonated amine-containing polymers such as protonated chitosan.

The phosphate derivatives of this invention are represented by the following formula:

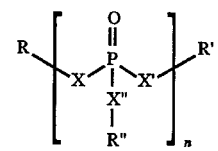

In the above formula:

R is selected from the group consisting of a coolant component, a sweetener component, and a flavorant component;

R' and R" are independently selected from the group consisting of R, an adherent component, M+, M++, C+, and hydrogen;

X, X', and X" are independently selected from the group consisting of oxygen, nitrogen, and sulfur; and n is an integer from 1 to 3.

In addition, R' may equal R", preferably wherein R' and R" are selected from the group consisting of calcium, zinc, magnesium, manganese, copper and stannous.

Preferred phosphate derivatives have the formula:

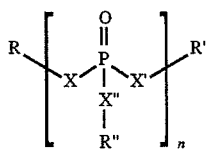

In the above formula:

R is selected from the group consisting of menthol, TK-10, WS-3, WS-23, MGA, methyl salicylate, acesulfame K, aspartame, saccharin, mannitol, sorbitol, neohesperidin dihydrochalcone, eugenol, vanillin, thymol, CGA, and linalool;

R' and R" are independently selected from the group consisting of R, C12–C18 diacyl glycerol, partially hydrolyzed vinyl acetate-ethylene co-polymer, cellulose, chitin, glucosamine, silica gel, glycerol, lower alkyl vinyl ether-maleic acids, sodium, potassium, calcium, zinc, magnesium, manganese, copper and stannous, ammonium, protonated amines, partially or fully protonated amine-containing polymers, and hydrogen;

X, X', and X" are independently selected from the group consisting of oxygen, nitrogen, and sulfur; and n is and integer from 1 to 3.

Structural examples of the above include, but are not limited, to the following:

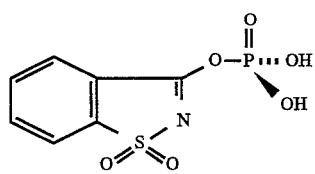

Saccharin Phosphate;

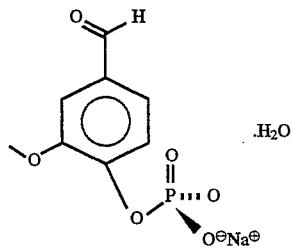

Vanillyl Monophosphate, Monosodium, Hydrate;

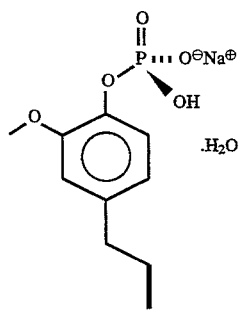

Eugenyl Monophosphate Monosodium Monohydrate;

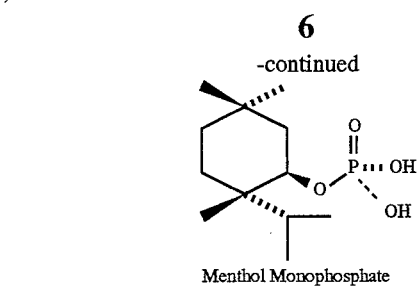

Menthol Monophosphate and

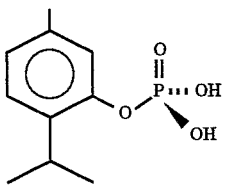

Thymol Monophosphate.

In addition, R' may equal R", preferably wherein R' and R" are independently selected from the group consisting of calcium, zinc, magnesium, manganese, copper and stannous.

Most preferred phosphate derivatives are menthyl monophosphate, eugenyl monophosphate, thymyl monophosphate, vanillyl monophosphate. The phosphate derivatives are used in the present invention at levels of from about 0.001% to about 25%, preferably from about 0.01% to about 15%, and most preferably from about 0.10% to about 5% by weight of the composition. Mixtures of the above described phosphate derivatives may also be used, improving the phosphate derivative activity.

These and other phosphate derivatives are further described in copending applications Ser. Nos. 07/855,989, filed Mar. 20, 1992 (WO/PCT 93/18741, published Sep. 30, 1993); 08/123,484, filed Sep. 17, 1993; 08/123,494, filed Sep. 17, 1993; 08/360,191, filed Dec. 10, 1994 and 08/306,868, file Sep. 15, 1994, all of which are herein incorporated by reference.

Copper Ion Source

Another essential component of the present invention is a compound providing a readily available source of copper ions. Compounds useful as such a copper ion source may be present in the compositions of the present invention at levels between about 1 and about 8000 ppm of copper ions. The preferred range being from about 25 to about 6000 ppm, with the most preferred range being from about 50 to about 4000 ppm. For dentifrices the preferred levels are from about 50 to about 8000 ppm, more preferably from about 100 to about 6000 ppm, and most preferably from about 100 to about 4000 ppm. For rinses the levels are preferably from about 25 to about 1000 ppm, more preferably from about 50 to about 750 ppm, and most preferably from about 50 to about 500 ppm. For lozenges and chewing gums levels as low as about 1 ppm copper are effective.

Suitable inorganic copper ion sources include copper chloride, $CuCl_2$, and the dihydrate thereof; copper fluoride, $CuF_2$ and the dihydrate thereof; copper fluorosilicate, $CuSiF_6$, and the hexahydrate thereof; copper sulphate, $CuSO_4$, and the pentahydrate thereof; copper nitrate and the tri- and hexa-hydrates thereof; and also less popular copper salts, such as copper bromide, $CuBr_2$; copper metaborate, $Cu(BO_2)_2$; copper bromate, $Cu(BrO_3)_2$; copper chlorate; $Cu(ClO_3)_2,6-H_2O$; copper iodate, $Cu(IO_3)_2$, copper fluorophosphate, $CuPO_3F$, or mixtures thereof.

Preferred copper salts of organic acids include copper acetate, copper formiate, copper benzoate, copper citrate, copper tartrate, copper lactate, copper malate, copper lysinate, copper mandelate, copper sorbate, copper pantothenate, copper gluconate, copper phytate, copper glycerophosphate, copper cinnamate, copper butyrate, copper propionate, copper laurate, copper oxalate, copper salicylate, copper glycinate, copper bis-glycinate or mixtures thereof. Mixtures of inoroganic or organic salts may also be used.

A preferred copper ion source for the compositions of the present invention is copper bis-glycinate. Copper bisglycinate is further described in U.S. patent application Ser. No. 08/096,535 to Mobley et al., filed Jul. 22, 1993, herein incorporated by reference.

Pharmaceutically Acceptable Carrier

The carrier for the active ingredient(s) herein can be any composition suitable for use in the oral cavity. Such compositions include toothpastes, mouthrinses, liquid dentifrices, lozenges, chewing gums or other vehicles suitable for use in the oral cavity. Toothpaste and mouthrinses are the preferred systems.

The abrasive polishing material contemplated for use in the toothpaste compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by W. R. Grace & Company, Davison Chemical Division. Preferred precipitated silica materials include those marketed by the J. M. Huber Corporation under the tradename, "Zeodent", particularly the silicas carrying the designation "Zeodent 119" and "Zeodent 128". A further description of silica abrasives suitable for use in the present invention are found in U.S. Pat. No. 4,340,583, Jul. 29, 1982, incorporated herein by reference.

The abrasive in the toothpaste compositions described herein is present at a level of from about 6% to 70%, preferably from about 15% to about 25%.

Flavoring agents can also be added to toothpaste compositions. Suitable flavoring agents include oil of wintergreen, oil of peppermint, oil of spearmint, oil of cloves or mixtures thereof. Additional flavoring agents useful in the compositions of the present invention apart from those mentioned as components of the phosphate derivatives include anise, cassia, anethole, dihydroanethole, ethyl maltol, estragole, menthol, para-hydroxy phenylbutanone, phenyl ethyl alcohol, sweet birch, thymol, eugenol, eucalyptol, cinnamic aldehyde, menthone, alpha-ionone, ethyl vanillin, vanillin, limonene, isoamylacetate, benzaldehyde, ethylbutyrate, cinnamaldehyde glycerol acetal ("CGA"), linalool, l-carvone, and mixtures thereof. Further examples of suitable flavoring agents are described in S. Arctander, *Perfume and Flavor Materials of Natural Origin*, (1960), herein incorporated by reference, and in the above mentioned Allure's Flavor and Fragrance Materials. Sweetening agents which can be used include aspartame, acesulfame K, saccharin, dextrose, levulose, xylitol, mannitol and sodium cyclamate. Flavoring and sweetening agents are generally used in toothpastes at levels of from about 0.005% to about 2% by weight.

Toothpaste compositions can also contain emulsifying agents. Suitable emulsifying agents are those which are reasonably stable and foam at a wide pH range, including non-soap anionic, nonionic, cationic, zwitterionic and amphoteric organic synthetic detergents. Many of these suitable agents are disclosed by Gieske et al. in U.S. Pat. No. 4,051,234, Sep. 27, 1977, incorporated herein by reference. The emulsifying agents are present at a level of from about 0.5% to about 10.0%.

Water is also present in the toothpastes of this invention. Water employed in the preparation of commercially suitable toothpastes should preferably be deionized and free of organic impurities. Water generally comprises from about 10% to 50%, preferably from about 30% to 50%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents in an amount from 0.2% to 5.0% by weight of the total composition can be used.

It is also desirable to include some humectant material in a toothpaste to keep it from hardening. Suitable humectants include glycerin, sorbitol, and other edible polyhydric alcohols at a level of from about 10% to about 70%.

Another preferred embodiment of the present invention is a mouthwash composition. Conventional mouthwash composition components can comprise the carrier for the agents of the present invention. Mouthwashes generally comprise from about 20:1 to about 2:1 of a water/ethyl alcohol solution or be alcohol free and, preferably, other ingredients such as flavors, sweeteners, humectants and sudsing agents such as those mentioned above for dentifrices. The humectants, such as glycerin and sorbitol give a moist feel to the mouth. Generally, on a weight basis the mouthwashes of the invention comprise 0% to 30% (preferably 0% to 5%) ethyl alcohol, 0% to 30% (preferably 5% to 30%) of a humectant, 0% to 2% (preferably 0.01% to 1.0%) emulsifying agents, 0% to 0.5% (preferably 0.005% to 0.10%) sweetening agent such as saccharin, 0% to 0.6% (preferably 0.03% to 0.3%) flavoring agent, and the balance water. Other optional components described herein earlier for use in toothpaste products are also useful in the mouthwash composition.

Suitable lozenge and chewing gum components are disclosed in U.S. Pat. No. 4,083,955, Apr. 11, 1978 to Grabenstetter, incorporated herein by reference in its entirety.

An additional optional ingredient for use in the compositions of the present invention is a soluble fluoride ion source. Such sources include sodium fluoride, stannous fluoride, sodium monofluorophosphate and are used in amounts sufficient to provide from about 10 to about 3500 ppm $F^-$.

Other optional components are non-cationic water insoluble agents such as triclosan. Such materials are disclosed in U.S. Pat. No. 4,022,889, to Vinson et al., incorporated herein by reference in its entirety.

The pH of the present compositions and/or the pH in the mouth can be any pH which is safe for the mouth's hard and soft tissues. Such pH's are generally from about 4.0 to about 9.5, preferably from about 4.5 to about 8.5. Buffers may be added to maintain this pH. Such buffers should, however, not complex with copper ions in a manner such that the functioning of the compositions of this invention is hindered.

A method of manufacture for the present compositions is found in the examples.

COMPOSITION USE

The present compositions are used in a conventional manner wherein the amounts of product are what users generally use.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES

Examples 1–5

Given below are five mouthrinse examples representative of the present invention.

| Component | Weight % | | | | |
|---|---|---|---|---|---|
| | Ex. 1 | Ex. 2 | Ex. 3 | Ex. 4 | Ex. 5 |
| Water | 70.86 | 87.41 | 69.15 | 62.38 | 73.13 |
| Sorbitol Solution (70% Aqueous) | 10.25 | — | — | 8.85 | 7.25 |
| Sodium Saccharin | 0.08 | 0.07 | 0.06 | 0.08 | 0.07 |
| Ethyl Alcohol | 10.60 | — | 18.74 | 14.48 | 12.20 |
| PEG 40 hydrogenated caster oil[1] | 0.46 | 0.75 | — | 0.34 | 0.57 |
| Sodium Alkyl Sulfate Soln (27.9%) | 0.75 | 0.75 | 0.60 | 0.60 | 0.75 |
| Copper Sulfate | 0.05 | 0.10 | 0.10 | 0.20 | 0.05 |
| Glycine | 0.03 | 0.06 | 0.06 | 0.12 | 0.03 |
| Peppermint Flavor | 0.24 | 0.20 | 0.19 | 0.16 | 0.20 |
| Glycerin | 6.18 | 10.26 | 10.45 | 12.35 | 5.37 |
| Eugenyl Monophosphate | 0.15 | — | — | 0.32 | — |
| Vanillyl Monophosphate | 0.35 | — | — | — | 0.38 |
| Thymyl Monophosphate | — | 0.40 | 0.20 | 0.12 | — |
| Menthyl Monophosphate | — | — | 0.45 | — | — |

[1]Available from BASF-Wyandotte, Parsippany, N.J. under the tradename Cremophor RH40.

Examples 6–10

Given below are five dentifrice examples representative of the present invention.

| Component | Weight % | | | | |
|---|---|---|---|---|---|
| | Ex. 6 | Ex. 7 | Ex. 8 | Ex. 9 | Ex. 10 |
| Water | 7.82 | 17.14 | 8.02 | 4.38 | 14.79 |
| Sorbitol Solution (70% Aqueous) | 54.27 | 46.86 | 52.45 | 58.48 | 47.25 |
| Sodium Saccharin | 0.37 | 0.40 | 0.30 | 0.38 | 0.35 |
| Sodium Fluoride | 0.24 | 0.24 | 0.24 | 0.24 | 0.24 |
| Carboxy Methyl Cellulose | 1.00 | 0.75 | 1.10 | 0.95 | 1.07 |
| Sodium Alkyl Sulfate Soln (27.9%) | 4.20 | 3.85 | 5.30 | 3.45 | 3.75 |
| Titanium Dioxide | 0.53 | 0.53 | 0.53 | 0.53 | 0.53 |
| Silica | 23.00 | 22.50 | 23.40 | 22.40 | 22.50 |
| Sodium Hydroxide (50% Soln.) | 0.22 | 0.22 | 0.10 | 0.10 | 0.22 |
| Copper Sulfate | 0.41 | 0.41 | 0.21 | 0.21 | 0.41 |
| Glycine | 0.24 | 0.24 | 0.12 | 0.12 | 0.24 |
| Peppermint Flavor | 1.20 | 1.10 | 1.05 | 1.16 | 1.20 |
| Glycerin | 5.30 | 4.86 | 5.68 | 6.25 | 3.95 |
| Eugenyl Monophosphate | 0.35 | — | — | 1.35 | 1.20 |
| Vanillyl Monophosphate | 0.85 | — | 1.00 | — | 0.80 |
| Thymyl Monophosphate | — | 0.90 | — | — | — |
| Menthyl Monophosphate | — | — | 0.50 | — | 1.50 |

| Component | Weight % | |
|---|---|---|
| | Ex. 11 | Ex. 12 |
| Water | 7.82 | 17.84 |
| Sorbitol Solution (70% Aqueous) | 54.27 | 46.86 |
| Sodium Saccharin | 0.37 | 0.40 |
| Sodium Fluoride | 0.24 | 0.24 |
| Carboxy Methyl Cellulose | 1.00 | 0.75 |
| Sodium Alkyl Sulfate Soln (27.9%) | 4.20 | 3.85 |
| Titanium Dioxide | 0.53 | 0.53 |
| Silica | 23.00 | 22.50 |
| Sodium Hydroxide (50% Soln.) | 0.22 | 0.22 |
| Copper Sulfate | 0.41 | 0.41 |
| Glycine | 0.24 | 0.24 |
| Peppermint Flavor | 1.20 | 1.10 |
| Glycerin | 5.30 | 4.86 |
| Menthyl Monophosphate | 1.20 | — |
| Saccharin Monophosphate | — | 0.20 |

What is claimed is:

1. An oral composition, comprising:

a) from about 0.001% to about 25% of at least one phosphate derivative having the structure:

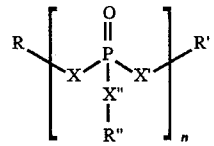

wherein R is a flavorant component selected from the group consisting of hexanol, octanol, decanol, geranolol, ethyl maltol, para-hydroxy phenylbutanone, phenyl ethyl alcohol, thymol, eugenol, eucalyptol, methyl salicylate, ethyl vanillin, vanillin, cinnamaldehyde glycerol acetal ("CGA"), or linalool;

wherein R' and R" are independently selected from the group consisting of R, an adherent component, $M^+$, $M^{++}$, $C^+$, and hydrogen;

wherein X, X', X" are independently selected from the group consisting of oxygen, nitrogen, and sulfur;

wherein n is an integer from 1 to 3;

b) a safe and effective amount of a copper ion source; and c) an pharmaceutically acceptable oral carrier.

2. An oral composition according to claim 1, wherein the phosphate derivative is selected from the group consisting of eugenyl monophosphate, vanillyl monophosphate, thymyl monophosphate, menthyl monophosphate and mixtures thereof.

3. An oral composition according to claim 2, wherein the phosphate derivative comprises eugenyl monophosphate and vanillyl monophosphate.

4. An oral composition according to claim 2, further comprising a flavoring agent selected from the group consisting of anise, cassia, clove, anethole, dihydroanethole, estragole, menthol, peppermint, para-hydroxy phenylbutanone, ethyl maltol, phenyl ethyl alcohol, sweet birch, thymol, eugenol, eucalyptol, wintergreen, spearmint, cinnamic aldehyde, menthone, alpha-ionone, ethyl vanillin, vanillin, limonene, isoamylacetate, benzaldehyde, ethylbutyrate, cinnamaldehyde glycerol acetal ("CGA"), linalool, l-carvone, and mixtures thereof.

5. An oral composition according to claim 4, wherein the concentration of the copper ion source is sufficient to provide from about 1 to about 8000 parts per million copper ions.

6. An oral composition according to claim 5, wherein the copper ion source is selected from the group consisting of copper bis-glycinate, copper gluconate and mixtures thereof.

7. An oral composition according to claim 6, wherein the orally acceptable carrier is a mouthrinse.

8. An oral composition according to claim 7, further comprising a humectant.

9. An oral composition according to claim 8, further comprising from 0 to about 30% ethanol.

10. A method of treating diseases of the oral cavity comprising the application of a safe and effective amount of a composition according to claim 1, to the teeth and other oral surfaces.

11. A method of treating diseases of the oral cavity comprising the application of a safe and effective amount of a composition according to claim 8, to the teeth and other oral surfaces.

* * * * *